United States Patent [19]

Weber et al.

[11] Patent Number: 5,284,654
[45] Date of Patent: Feb. 8, 1994

[54] METHOD FOR THE TREATMENT OF PARKINSON'S DISEASE

[75] Inventors: Richard J. Weber, Silver Spring; Robert J. Plunkett, Gaithersburg, both of Md.; Scott E. Ewing, Chicago, Ill.

[73] Assignee: The United States of America as represented by the Department of Health and Human Services, Washington, D.C.

[21] Appl. No.: 892,485

[22] Filed: Jun. 3, 1992

Related U.S. Application Data

[63] Continuation of Ser. No. 401,141, Aug. 31, 1989, abandoned.

[51] Int. Cl.⁵ ............................................. A61K 35/14
[52] U.S. Cl. ................................................ 424/93 V
[58] Field of Search ............... 424/93 V; 435/2, 240.2

[56] References Cited

U.S. PATENT DOCUMENTS 4,902,288  2/1990  Ingram .................................. 424/534

OTHER PUBLICATIONS

LeFur et al, Biol. Abstracts, vol. 73 (1981), 4433.
Sladek et al, in Ann. N.Y. Acad Sci., vol. 495 (1987) pp. 641–657.
Backlund et al, in Ann. N.Y. Acad. Sci., vol. 495 (1987) pp. 658–669.

*Primary Examiner*—Jacqueline Stone
*Attorney, Agent, or Firm*—Office of Technology Transfer, National Institutes of Health

[57] ABSTRACT

The present invention is directed to a method for the treatment of Parkinson's disease which affect the dopaminergic system by implanting into the brain of a host in need thereof an anti-neurodegenerative effective amount of activated leukocytes.

3 Claims, 1 Drawing Sheet

METHOD FOR THE TREATMENT OF PARKINSON'S DISEASE

This application is a continuation of application Ser. No. 07/401,141 filed on Aug. 31, 1989, now abandoned, the entire contents of which are incorporated herein by reference.

BACKGROUND OF THE INVENTION

Parkinson's disease is a dopaminergic neurodegenerative disorder which afflicts an estimated 1% of the population over the age of fifty. The disease is primarily characterized by tremor, rigidity, impaired postural reflexes, and paucity of movement resulting from the loss of dopaminergic neurons in the substantia nigra which normally project to the corpus striatum. Because parkinsonian patients have a low concentration of dopamine in this region of the basal ganglia, current therapies have been directed at restoring normal levels of dopamine using the dopamine precursor L-dopa, with a peripheral decarboxylase inhibitor such as carbidopa. However, L-dopa's effectiveness diminishes with continued use and troublesome side effects often occur. Thus, alternative therapies are being sought. Strategies to promote functional recovery by implantation of fetal dopaminergic cells in specific dopamine-depleted areas of the brain are currently being evaluated in Parkinsonian animal models as well as in certain patients with Parkinson's disease. No doubt this investigational treatment will be confronted with some opposition on moral grounds.

The present invention has been accomplished with the above disadvantages in mind.

SUMMARY OF THE INVENTION

The present invention is directed to a method of treating neurodegenerative disorders which affect the dopaminergic system by implanting into the brain of a host in need thereof an anti-neurodegenerative effective amount of activated leukocytes.

DETAILED DESCRIPTION OF THE PREFERRED EMBODIMENTS

Figure 1:
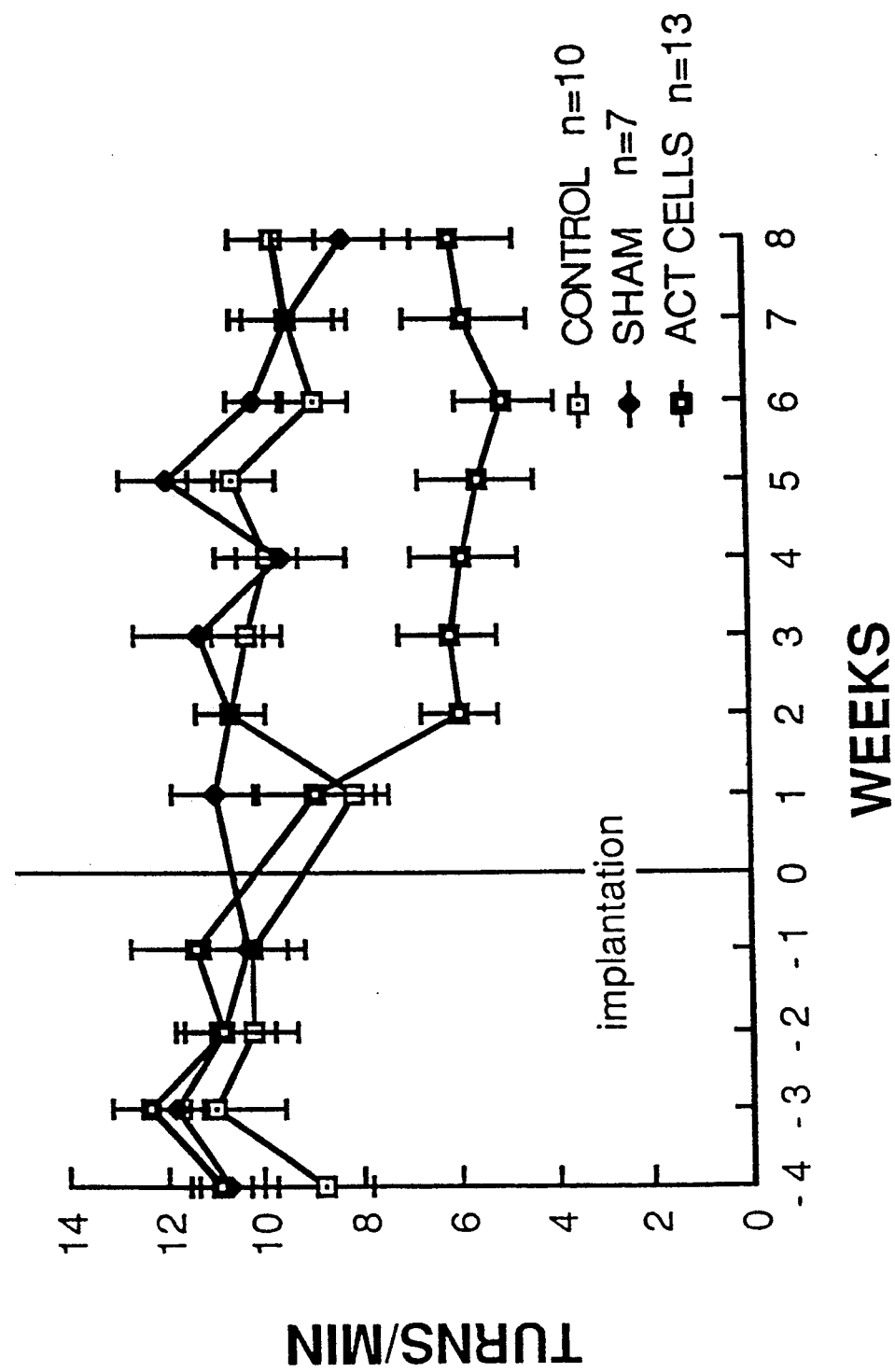
FIG. 1 is a graph which shows the results of testing for amphetamine induced rotation during a period of 13 weeks which followed implantation of the activated leukocytes of the present invention.

By dopaminergic neurodegenerative disorders is meant those disorders which affect the dopaminergic system, e.g., Parkinson's Disease and other such diseases which result in a loss of CNS regulated function.

By host is meant any patient afflicted with such conditions, including humans, and is in need of said therapy. The leukocytes to be utilized from the present invention should be histo-compatible. Preferred leukocytes are autologous tissue.

The leukocytes of the present invention are activated by conventional means known in the art where the known activators are brought into contact with the cells. Examples of known activators are plant mitogens, lymphokines and cytokines as are described in William E. Paul, *Fundamental Immunology*, Raven Press, New York, 1984, page 271-274 and page 299. Examples of mitogens useful in activating the leukocytes to be utilized in the present invention are phytohemagglutinin (PHA), Sigma Chemicals Company, St. Louis, Mo.; lipopoly-saccharide (LPS), Difco Laboratories, Detroit, Mich.; and pokeweed mitogen (PWM). Examples of the lymphokines useful in activating the leukocytes to be utilized in the present invention are interleukin-2 (IL-2), Cetus Corporation, Calif.; and interleukin-3 (IL-3), Genzyme Corp., Boston, Mass. Examples of cytokines useful in activating the leukocytes utilized in the present invention are interleukin-1 (IL-1) and tumor necrosis factor (TNF), etc., both obtained from Collaborative Research, Lexington, Mass.

The activated leukocytes can be administered to the locus of the lesion by surgical implantation in a one time or a number of surgical implantations sufficient to elicit the desired response. The dosage amount to be implanted can be from about $1 \times 10^5$ to $1 \times 10^7$ cells. The cells can be administered in any known pharmaceutically conventional carrier such as normal saline. The dose, of course, will vary from patient to patient, depending on the severity of the lesions and/or the disease state and can readily be ascertainable by one skilled in the art.

The leukocytes can be activated either in vivo or in vitro. When activated in vitro, the thus produced activated leukocytes are surgically implanted to the lesioned area of the brain. When treating humans the leukocytes could be activated in vitro. In case of Parkinson's Disease the locus of the lesion is known to be in the striatum.

The present invention overcomes a number of disadvantages associated with the prior art therapies. For example, with respect to L-Dopa therapy, the present invention can reduce or totally eliminate L-Dopa therapy, thus decreasing or eliminating the untoward side effects associated therewith. The present therapy would also be an alternative to fetal implantation therapy, thus eliminating any moral issues raised by such a therapy.

Since in most instances it would be the patients' own auto-logous leukocytes which are activated, the cells to be utilized in the surgical procedure would be readily available and the chances of host rejection would be slim to none.

EXPERIMENT 1

Thirty adults, male Sprague-Dawley rats that had undergone prior superior cervical ganglionectomies were made hemiparkinsonian by selectively lesioning the pars compacta of the substantia nigra as described by Paresi et al., *Brain Research*, Vol. 494, pg. 286 (1989). The incisor bar on a Kopf stereotaxic frame was set at 3.3 mm below horizontal zero and two sites were injected. Coordinates for the first injection were A 3.5 mm, L 1.9 mm, and V 7.1 mm with respect to the right base of lambda and the dura (bevel rostral); coordinates for the second injection were A 3.5 mm, L 2.3 mm, and V 6.8 mm, respectively (bevel lateral). Injections were made at 1 µl/min using a 10 µl Hamilton syringe equipped with a 26s needle; the needle was left in place for at least 10 minutes before being withdrawn at 1 mm/min. Six micrograms (calculated as base) of 6-OHDA hydrobromide (Sigma) dissolved in 0.9% saline containing ascorbic acid (0.2 mg/ml) was injected in a volume of 3 µl at the first site; 8 µg in a volume of 4 µl was injected at the second site.

The dopaminergic neurons of the ventral tegmental area of the mesencephalon are spared by this method which produces a degree of neurodegeneration similar to idiopathic Parkinson's disease in humans. 6-hydroxydopamine (6-OHDA), a catecholaminergic neurotoxin, was stereotactically injected into the pars compacta of the right substantia nigra following anesthesia with 350 mg/kg of chloral hydrate administered intraperitoneally. Ten days after lesioning, rats were tested for rotational behavior induced by D-amphetamine, a dopamine releasing agent. Rats in which the dopaminergic nigrostriatal pathway has been unilaterally destroyed rotate toward the side of the lesion when given amphetamine. The number of full body clockwise and counterclockwise turns of each rat was recorded in a rotameter as described by Ungerstedt, Brain Res, 24,485 (1970). Rats turning consistently at least 7 clockwise turns/min over a 90 minute period for 4 trials, which reflects a 98% or greater denervation of the striatum on the lesioned side were divided into three groups: unimplanted ($n=10$), sham-implanted ($n=7$), and implanted ($n=13$).

EXPERIMENT 2

Rats in the sham-implanted and implanted groups received 5 microliter stereotaxic injections of medium or a total of $3-7 \times 10^5$ activated leukocytes respectively, aimed at the following coordinates: A 0.20 mm, V 5.4 mm, L 2.2 mm (bevel rostral); A 0.20 mm, V 6.4 mm, L 3.2 mm (bevel rostral); A 1.60 mm, V 5.2 mm, L 2.0 mm (bevel rostral); A 1.60 mm, V 5.2 mm, L 2.8 mm (bevel caudal), using the technique described by Plunkett et al., J. Neurosurg. 69, 228 (1989). The needle was left in place for 2 min before being withdrawn at 1 mm/min. R. J. Plunkett, R. J. Weber, E. H. Oldfield, J. Neurosurg. 69, 228 (1989). The leukocytes were lavaged with 0.32M sucrose from the peritoneal cavity of normal Sprague-Dawley rats which had been injected intraperitoneally 48 hours earlier with 1 mg phytohemagglutinin (PHA). Analysis of the activated leukocytes by flow cytometry are described in Weber et al., Cell Immunology, 104, 400 (1978) revealed predominantly macrophages and T-lymphocytes. Monoclonal mouse IgG1 antibody to Thy 1.1, clone OX-7 culture supernatant and monoclonal mouse IgG2A antibody to rat macrophage antigen OX 41 ascites fluid were purchased from Pel-Freeze Biologicals (Rogers, AR); Fluorescein-labeled affinity-purified goat antibodies to mouse IgG(H+L) adsorbed with rat serum were purchased from KPL Laboratories, Inc. (Gaithersburg, Md.). Trypan blue exclusion immediately after harvesting and during the period of implantation confirmed cell viability ($>95\%$).

FIG. 1 shows the results of all three groups which were tested weekly for amphetamine-induced rotation during the 13 weeks following implantation. Turning decreased an average of 47% at 8 weeks in the rats implanted with leukocytes ($p=0.006$; Wilcoxon signed rank). As can be seen by FIG. 1 neither the rats in the sham-implanted group nor those in the control group showed a significant decline in turning. Improvement was rapid in the implanted rats, with an average decrease in amphetamine-induced rotation of 22% one week after implantation. In the two rats showing complete improvement, recovery was noted by the fourth and fifth week. Only two of the rats receiving leukocytes failed to show an increase in dopamine content or TH reactivity.

Punch biopsies were taken from the rostral striatum in 8 rats that failed to improve behaviorally (2 shams, 4 controls, and 2 unimproved implanted rats). Identical biopsies were taken in 7 of the leukocyte-implanted rats that improved. Dopamine content of the lesioned right striatum was determined by high performance liquid chromatography to be 0.1% of the intact left striatum in unimproved implanted rats. The results are reported in Table I below.

TABLE I

| | | DOPAMINE LEVELS (pcg/mcg protein) (mean ± sem) | | |
|---|---|---|---|---|
| | | Right caudate | Left Caudate | R/L |
| I. | Control (4) | 3.0 ± 1.8 | 103.3 ± 20.4 | 2.9 |
| II. | Sham (2) | 1.5 ± 0.6 | 91.4 ± 33.8 | 1.6 |
| IIIa. | Implant (7) Improved | 4.5 ± 1.3 | 67.4 ± 13.3 | 6.7 |
| IIIb. | Implant (2) Unimproved | 0.1 ± 0.01 | 131.6 ± 14.2 | 0.1 |

The dopamine content in the right striatum of rats implanted with leukocytes was restored to 6.7% of the left striatum.

Previous studies have shown that dopamine-rich grafts can provide complete compensation of amphetamine-induced turning in 6-OHDA lesioned rats and restore dopamine levels to 10-15% of normal. The results reported herein show here that stereotaxically implanted leukocytes alone may be sufficient to bring about behavioral recovery.

All reference articles discussed, supra, are incorporated herein by reference.

While the invention has been described with regard to certain preferred embodiments, it is understood that various changes and modifications may be made without departing from the scope of the invention which is defined in the Claims.

We claim:

1. A method for treating the dopaminergic neurodegenerative disorder Parkinson's Disease by administering to a locus of a lesion of a patient suffering from said disorder an anti-neurodegenerative effective amount of in vitro activated leukocytes.

2. The method according to claim 1, wherein said anti-neurodegenerative effective amount is from about $1 \times 10^5$ to $1 \times 10^7$ cells.

3. The method according to claim 1, wherein said leukocytes are derived from said patient suffering from said dopaminergic neurodegenerative disorder.

* * * * *